United States Patent [19]

Shah

[11] Patent Number: 5,469,863
[45] Date of Patent: Nov. 28, 1995

[54] POLYURETHANE CONDOM OF WELDED POLYURETHANE FILM

[75] Inventor: Tilak M. Shah, Cary, N.C.

[73] Assignee: Polygenex International, Inc., Cary, N.C.

[21] Appl. No.: 104,666

[22] Filed: Aug. 11, 1993

[51] Int. Cl.⁶ .................................................. B32B 31/00
[52] U.S. Cl. ..................... 128/844; 156/272.2; 156/274.4
[58] Field of Search ......................... 128/844; 156/272.2, 156/274.4

[56] References Cited

U.S. PATENT DOCUMENTS

| | | | |
|---|---|---|---|
| 4,852,586 | 8/1989 | Haines | 128/844 |
| 5,024,852 | 6/1991 | Busnel et al. | 128/844 |
| 5,191,902 | 3/1993 | Wilk | 128/844 |
| 5,335,675 | 8/1994 | Wheeler | 128/842 |

FOREIGN PATENT DOCUMENTS

| | | | |
|---|---|---|---|
| 1026044 | 3/1958 | Germany | 128/844 |
| 59-211448 | 11/1984 | Japan | 128/844 |

*Primary Examiner*—Chester T. Barry
*Attorney, Agent, or Firm*—Waldron & Associates

[57] ABSTRACT

A method of welding at least two layers of a thin thermoplastic polyurethane elastomer (10A, B) to form a weld seam (12) to produce polyurethane barrier products such as, but not limited to, gloves (20), condoms (30), inflatable catheter balloon cuffs (48A, B), ostomy pouches (50), organ bags (60), and instrument covers (70) through a process of pre-heating a sealing die platen, the at least two layers of the polyurethane (10A, B) softened while under pressure from the preheated die platen, followed by welding the at least two layers of polyurethane (10A, B) film by transmission of a radio-frequency energy to the film (10A, B) to produce a weld seam (12) and then allowing the weld seam (12) to cool, the resultant product having seam integrity.

8 Claims, 6 Drawing Sheets

POLYURETHANE CONDOM OF WELDED POLYURETHANE FILM

BACKGROUND OF THE INVENTION

1. Field of the Invention

The present invention relates to a new method of joining by a welding process, at least two layers of a thin polyurethane thermoplastic elastomer film having a thickness in the range of 0.5 to 5.0 mils (0.0127 mm to 0.127 mm), without wrinkling, causing pin-holes or holidays and without burning or charring the material. Such welded polymer films are employed to make gloves, including industrial and medical gloves, condoms, organ bags for endoscopic surgical procedures, catheter balloons, and barrier structures to isolate articles, including medical and surgical instruments from environmental contamination, infectious material and the like.

2. Description of Background and Other information

Natural rubber sheet and film, formed by coagulation of natural rubber latex, have long been employed to form barrier and environmental protective products, such as surgical gloves, condoms, and the like.

In the medical and surgical field, there is a substantial need for effective and reliable infection and contaminant-control barrier products, primary among which are surgical gloves. These products must not leak or rupture nor must there be any breach of the barrier material through porosity, permeability or structural weakness. Desirably, such products should provide protection against accidental cuts and needle sticks, and the like. A long shelf life before use is important, as are physical properties such as resistance to tearing, solvents and other environmental exposure. These features should desirably be attained in products which are thin enough to present minimal interference with tactile sensing and mobility.

Industrial gloves and related barrier apparel and clothing and the like have similar requirements.

Condoms are of increasing importance in the prevention of the spread of AIDS viruses, other sexually transmitted diseases, and for effective contraception.

The use of containment for excised tissue and organs in surgical procedures is also of increasing import in the medical field, particularly in the fast growing field of endoscopic examination and surgery. For example, in the removal of a gall bladder, appendix or other organ or tissue suitable to an endoscopic approach.

Catheter balloons are important in procedures such as angioplasty and in the use of in-dwelling catheters, endotracheal tubes and other devices where an inflatable cuff is required.

Barrier containment for implantable devices, such as cardiac pacemakers and the like, and for surgical instruments inserted into the body during surgical procedures is another area of increasing importance. For example, difficult to clean and sterilize instruments such as liposuction cannulae, endoscopic instruments and other lumen containing and complex instruments where cleaning and sterilizing may be unreliable.

These are products which require thin film or sheet materials, and are frequently made of natural rubber or "latex" film and sheet materials.

Latex sheet or film is normally a porous material with a certain amount of permeability. Latex products are often formed through a dipping technique which, as the latex becomes thinner or is stretched, results in an increase in porosity and permeability. Comparable limitations apply to milled sheets formed on rolling or rubber mills. Certain chemicals and molecules, up to the size of AIDS viruses, can permeate latex without causing rupture or displacement, an undesirable characteristic in barrier protection. Latex cannot provide barrier integrity for devices such as surgical gloves and condoms where barrier protection is of prime importance.

Latex also has limited tensile strength and tear resistance and is highly susceptible to cuts and punctures. In addition, the material has a limited shelf life, and will become more fragile and brittle over time.

In today's society, barrier products require maximum protection to prevent the spread of pathogenic organisms as well as the preventing contamination of otherwise clean or sterile materials or devices. Latex products cannot provide this quality of protection because of material faults inherent in the material formed by available techniques.

There is an increasing proportion of the population of potential latex users, particularly workers in the medical and related fields, that are unable to use latex products because of an allergenic reaction that contact with latex products produce in sensitive individuals. Increasing reports are appearing in the medical literature of anaphylactic shock reactions attributed to exposure to latex products, as well as less serious but quite irritating contact dermatitis. As a result of the frequency and severity of such problems, OSHA regulations and guidelines have recently been established requiring employers to provide workers exposed to blood borne pathogens with an adequate hypo-allergenic substitute or other effective alternatives to contact with natural rubber latex products.

In addition, the contact dermatitis that occurs as a result the customary employment of lubricants and powders with latex products can be severe, painful and require treatment.

Synthetic polymer elastomers are finding a greater use in applications traditionally supplied by latex for rubber goods, both in the medical/surgical fields, and in a variety of commercial and industrial applications.

It has been recognized that polyurethane polymers have properties desirable for many of the rubber goods heretofore made of natural rubber, particularly thermoplastic elastomer polyurethanes.

There has been considerable effort in the industry to provide barrier device products of polyurethane materials as a substitute for latex, but until now, no cost effective and fully reliable method to produce such products has been available.

The dipping technique employed for many natural rubber latex products can be employed with polyurethanes, but have not attained all the advantages and benefits desired. For example, dipping processes are expensive, because of the expensive solvents and the attendant environmental and atmospheric pollution and fire and health concerns required to form and deal with dipping solutions of polyurethanes, while the nature of dipping processes does not produce optimal film properties in any event. It is difficult to attain dip molded films which are reliably free of pin holes and porosity. It is also difficult to achieve uniform film thicknesses required of a number of uses.

Some polyurethane products are formed by joining polyurethanes with the use of adhesive bonding or welding techniques. However, most effective adhesives are poorly tolerated or are completely intolerable in many contexts of use, and are time and labor intensive operations, while welding techniques have been limited to joining layers of polyurethane having a thickness of no less than about 5 mils (0.127 mm).

Until the present invention, the welding of thin layers of polyurethane in the range of 0.5 to 5.0 mils (0.0127 to 0.127 mm) resulted in wrinkles, pin holes, discontinuities, holidays and burn or charring defects. The use of thin polyurethane film has been precluded because of the lack of a safe and a reliable welding method that preserved the integrity of the seam formed by the weld while creating a seam that was of high quality acceptable to users.

The joining of polyurethane to form a seam is well known in the art. Methods such as adhesive bonding, electromagnetic bonding, hot plate welding, induction bonding, insert bonding, radio-frequency sealing, spin welding, thermostacking, ultrasonic sealing and vibration welding have all been described in the literature. None of these methods, however, provide a secure, reliable and reproducible seam where the polyurethane is in the form of a film with a thickness in the range of 0.5 to 5.0 mils (0.0127 to 0.127 mm) and, therefore, are not applicable to polyurethanes less than 5 mils (0.127 mm) in thickness. As those of ordinary skill in the art will recognize, these are the very dimensions of greatest interest fin a very substantial proportion of uses and products.

Generally, the welding of thin polyurethanes, due to the thinness and broad melting point temperature of the material, resulted in several problems, including:

1) film wrinkling during welding;
2) seam pin holes or holidays;
3) too broad of a seam;
4) arcing, charring and burn marks of the polyurethane;
5) risk to the manufacturing operator; and
6) unacceptable levels of failure in use.

There are several problems with current joining, bonding or welding methods in their application to thin polyurethanes. For example, with conventional heat sealing equipment, it is difficult to control temperature accuracy due to a temperature rise with a longer time use. Because of this lack of temperature uniformity critical in thin film joining, wrinkling, pin holes or holidays can occur in the seam.

Electromagnetic bonding for thermoplastic substrata is based on the principle of induction heating: a composition consisting of ferromagnetic particles dispersed in a polymer matrix develops heat when subjected to a high-frequency alternating current source. When this composition is placed between two synthetic polymer elastomers, the heat developed is used to rapidly fuse the abutting surfaces. The technique is limited to thick structures, greater than 5 mils in thickness. In many contexts, the presence of ferromagnetic particles is unacceptable.

Impulse heating creates an unacceptably broad seal. When the material to be sealed is thin, pin holes and holidays result due to uneven and poor temperature control. A sufficient seal cannot be assured and reproducibility is poor.

Radio-frequency welding is also known as R.F. heat sealing, high-frequency sealing, or dielectric heat sealing. A radio-frequency welder directs a large: amount of radio frequency energy into the seam area. The energy causes the molecules of the material to oscillate or vibrate, creating heat. A combination of this heat, and pressure exerted by the pressure component of the welder, causes the materials to fusion bond. The ability and ease at which materials bond is related to their dielectric properties. Radio-frequency bonding works well when the thickness of a thermoplastic polyurethane elastomer film is greater than 5.0 mils (0.127 mm) although the energy intensity required is rather high. In thin film applications, sparking occurs due to arcing which can cause burns and chars to the film. This can also be hazardous to the operator. Radio-frequency welding is not widely employed with thermoplastic polyurethane elastomers because of these limitations.

The most commonly used application of radio-frequency welding is in polyvinyl chloride bonding and embossing in which the melting of the material brought about by molecular vibration. Molecules within the material are subject to periodic stresses caused by a radio frequency field alternating in polarity several million times per second, most often at 27.12 MHz. The amount of heat developed in the material is directly proportional to the amount of radio-frequency power applied to it. If the material has a high dissipation factor, that enables a rise in temperature in a radio-frequency field, when the heat exceeds the melting point of the material under pressure, and such a melt, under control, can be employed to form a fusion bonded joint or weld.

Until now, it has not been possible to convert, particularly for surgical and medical use, the excellent properties of thin thermoplastic polyurethane elastomer materials with a thickness of less than 5 mils (0.127 mm) into effective rubber goods. While polyurethane has been available for many years, the ability to produce thin polyurethane safe and usable barrier products having acceptable seam integrity has not been available. Polyurethanes have properties superior to latex, including structural strength, elasticity and the absence of porosity and permeability.

U.S. Pat. No. 4,463,156 to McGary, Jr. et al., "Polyurethane Elastomer and an Improved Hypoallergenic Polyurethane Flexible Glove Prepared Therefrom", discloses a soft, low modulus, non-crystalline segmented polyurethane glove comprised of specific chemical and physical characteristics that result in a more comfortable and easier to use surgical glove. McGary, Jr. et al. do not suggest or teach a method of joining two layers of thin polyurethane film to form a weld seam through the process of radio-frequency welding in glove fabrication.

U.S. Pat. No. 3,148,235, "Method of Making Plastic Gloves", and U.S. Pat. No. 3,197,786, "Plastic Gloves" to Velonis, disclose a method for making a seamless plastic glove and the glove itself, formed from a film of a fused polyvinyl chloride resin by utilizing dipping forms made from aluminum. The method and product of Velonis does not suggest or teach a method of joining two layers of thin polyurethane film to form a weld seam through radio-frequency welding in glove fabrication.

U.S. Pat. No. 4,684,490 to Taller et al. "Process for Preparation of Polyurethane Condoms", discloses a polyurethane condom formed through a dipping method in which the polyurethane is in the form of an organic solvent solution. The process of Taller et al. does not anticipate or teach a method of joining two layers of thin polyurethane film to form a weld seam through radio-frequency welding in condom fabrication.

U.S. Pat. No. 3,553,308 to Kobayashi et al., "Method for Preparing Polyurethane Molded Articles", is a method in which articles, particularly condoms, are prepared by alternately dipping a condom mold, at a controlled speed, in a polyurethane prepolymer solution and then curing the solution. Kobayashi et al. do not teach or suggest a method of joining two layers of thin polyurethane film to form a weld seam through radio-frequency welding in fabricating a condom.

U.S. Pat. No. 4,576,156 to Dyck et al., "Prophylactic Device and Method", discloses a method of preparing a condom in which a thermoplastic polyurethane elastomer material is deformed using a preformed mandrill in which a vacuum is applied to the system during the deformation step. Dyck et al. does not teach or suggest a method of joining two layers of thin polyurethane film to form a weld seam through radio-frequency welding in producing a condom.

U.S. Pat. No. 3,094,704 to Abildgaard, "Plastic Glove", discloses a seamless plastic glove made from a skin-fitting form-mold plastic layer is produced from an elastomer by spraying a molten or dissolved plastic material on a plurality of molds or forms. Abildgaard does not teach or suggest a method of joining two layers of thin polyurethane film to form a weld seam through radio-frequency welding in the production of gloves.

As has been noted, seam integrity is an essential and critical parameter for barrier devices in preventing the transmission of microscopic particles or for special sensor devices to prevent electrolyte transmission prematurely.

SUMMARY OF THE INVENTION

We have found that highly efficient R.F. welding of thermoplastic polyurethane elastomers is attained by heating the polymer to a temperature above the Vicar softening temperature (but below the heat distortion temperature or film distortion temperature), and subjecting the heated polymers to be joined to R.F. energy and pressure. The invention is particularly useful for joining thin films of the polyurethane, particularly films of 0.5 to 5.0 mils (0.0127 to 0.127 mm).

The R.F. welding technique is employed to fabricate a variety of medical and industrial products, including gloves, condoms, catheter balloons, containments for implantable medical appliances and devices, endoscopic tissue and organ containment bags, cavity liners for surgical and medical implements such as liposuction cannulae, and the like.

BRIEF DESCRIPTION OF THE DRAWINGS

The above and additional objects, characteristics, and advantages of the present invention will become apparent in the following detailed description of preferred embodiments, with reference to the accompanying drawings.

DETAILED DESCRIPTION OF THE DRAWINGS AND PREFERRED EMBODIMENTS

Figure 1:
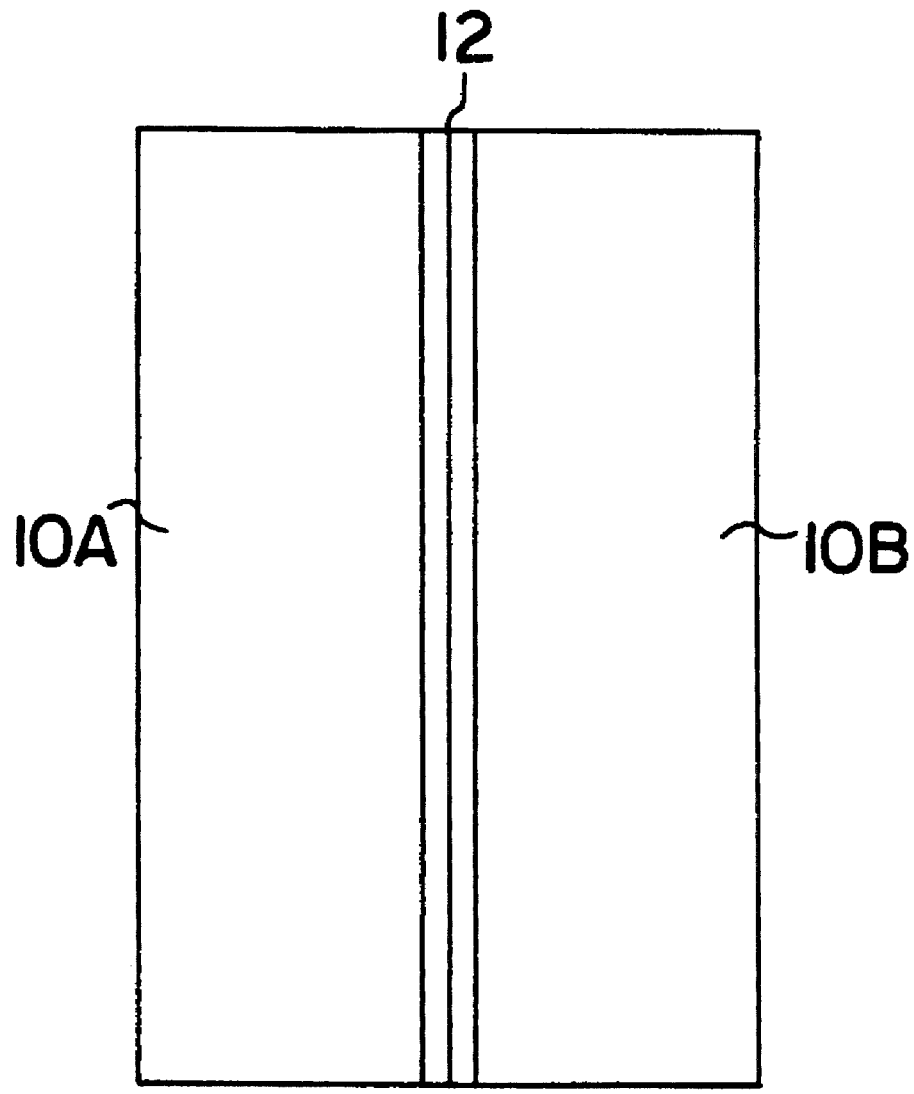
FIG. 1 is a top view of two welded thin film layers of a thermoplastic polyurethane elastomer material.

The present invention is a new method of making rubber goods from thin layers of thermoplastic polyurethanes and the thin thermoplastic polyurethane rubber goods to be used as barrier products and devices in a variety of medical, commercial and industrial fields. The products of this new method have high integrity, and are free from wrinkles, pin holes, holidays, burns or charring, mandatory in devices of this class.

This new method combines the use of heat from a preheated die platen with a radio-frequency welding technique to create a uniform weld seam in a thin polyurethane film material having a thickness in the range of 0.5 to 5.0 mils (0.0127 to 0.127 mm).

In using contact conduction heat-sealing equipment, heat is transferred from the edge of the outer layer to the inner layer of the film. This typically results in a temperature gradient in the two layers of film with a difference in temperature between the layers. When used on thin film, a wrinkling occurs at the seam accompanied by the formation of the formation of pin holes and holidays due to the uneven heat. The thinness of the film exacerbates the effects.

In using the technique of radio frequency welding alone, heating takes place throughout the polymer layer. The molecular layer at the interface of two layers becomes excited and generates heat. Once the energy is input the heat raises the temperature to the fusion point, thus creating the seam in conjunction with applied pressure. Because the effect operates at the molecular level, radio-frequency welding achieves excellent seam integrity and the technique is sometimes used for polyurethane film thicknesses greater than 7.0 mils (0.177 mm) in thickness. However, in the film thickness range of 0.5 to 1.5 mils (0.0127 to 0.0381 mm), there is very slow absorption of the radio-frequency energy required to give enough heat to achieve seam integrity becuase of the microcrystalline character of the polymer. At the required radio-frequency energy level, the energy will induce the arcing and spark that results in burn holes in thin film. It can also create a char, and may damage the die platen itself. R.F. welding of thin polyurethane films, less than about 5 mils in thickness, is not employed for these reasons.

In the broadest terms, the present invention is based on the discovery that R.F. welding of thermoplastic polyurethanes, and in particular, thermoplastic polyurethane elastomers, is highly efficient if conducted above the polymer Vicar softening temperature. Thus, preheating the polymer to an appropriate temperature, placing polyurethane parts to be joined in joining configuration under pressure, and applying radio-frequency energy to the joint region can be effectively and efficiently employed to form high quality welded joints at greater efficiency and economy than has heretofore been possible.

It is, of course, apparent that the invention has its greatest utility in the welding of very thin films of thermoplastic polyurethane, on the order of 0.5 to 5.0 mils (0.0127 to 0.127 mm) in thickness, which have not been amenable to effective and reliable welding by other techniques, including normal R.F. welding procedures. Thus, while the technique is equally applicable to thicker films and other forms of such polymers, the present invention is hereafter discussed with primary reference to the fabrication of welded joints and seams between these very thin films.

Most molecules are polarizable in an electric field. The degree of polarization, and the energy required to achieve it, is controlled by the dissipation factor or loss factor of a material. A material that is readily polarized by a small electric field has a high loss factor and is easy to heat.

As polarizing field alternates direction at a high frequency, considerable energy can be imparted to each molecule of the material. A very large number of materials are resonant at the usual frequency of 27.12 MHz commonly employed for R.F. welding. Thermoplastic polyurethanes are no exception.

This energy appears as heat. Since the electrical field penetrates the material, the heat is generated within the material and radiates or transfers outwardly.

The amount of heat generated without arcing or interior scorching is dependent on the dielectric properties and the "dissipative factor" and "loss index" of any particular material.

Following equation defines the power input and rate of heat generation:

$$P = 2\pi f E^2 C \epsilon' \tan \sigma$$

wherein:

P=power input in W f=frequency (normally, 27.2 MHz for R.F. welding)

E=field strength or voltage between the electrodes Kv

C=capacitance of the material in pF $\epsilon$=dielectric content tan $\sigma$32 the loss factor ($\epsilon'$)×(tan $\sigma$)=dissipation factor (for $\sigma \geq$ loss index)

The higher the loss index, the easier a material is to heat.

Thick (8 mil and above) plasticized polyvinyl chloride film is well known to be suitable but not optimal for R.F. welding techniques. Thick polyurethane films are welded by R.F. energy. However, polyurethane films require three to four times more power than polyvinyl chloride films of comparable thickness.

These differences in power input requirements stem from several major factors:

Polyvinyl chloride has the readily polarizable C1 group on the polymer chain. Polyurethanes do not commonly have such substituents.

In addition, polyvinyl chloride is highly plasticized in almost all its common forms while polyurethanes—particularly in film form—generally are not plasticized at all or have modest levels of such additives.

Polyurethanes in the form of thermoplastic elastomers are dependent on microcrystalline domains to provide their elastomeric properties. The amount of such microcrystallinity is variable with processing techniques and is generally highest in films, ordinarily formed by blowing techniques. The blown films are more highly ordered and oriented by the stretching of the film during blowing. The thinner the film, the higher the microcrystalline content of the film.

The crystalline domains have low dissipation factors which increases the R.F. energy input required for heating. The heat input requirements are directly proportional to the amount of microcrystallinity. During R.F. heating, a substantial component of the input is required to raise the temperature of the crystalline domains to an adequate temperature to achieve a dissipation factor comparable to the amorphous regions in the polymer (at and above the Vicat softening temperature).

Typically, a polyurethane thermoplastic elastomer film will require a power input three times higher than a polyvinyl chloride film of comparable thickness to attain R.F. welding bonds. Attempting to do so at high energy input results in qualitative problems of arcing, sparking, charring, bond discontinuities or "holidays" and the like.

While many of the difficulties could be resolved by reducing the energy level of the R.F. input, the time to achieve bonding temperatures is materially and unacceptably increased, and the productivity of R.F. welding and the justification for the capital costs is lost.

In our invention, the thermoplastic polyurethane elastomer is heated to a temperature above the Vicar softening temperature of the polymer prior to the R.F. welding procedure. The Vicar softening temperature of such elastomers is ordinarily in the range of about 60° C. to 150° C. These temperatures are conveniently attained by a wide variety of techniques, from preheating the material in an oven, to passing the material, particularly in film form, under infrared heat lamps, to conducting the R.F. welding with a heated platen and die. The latter is generally preferred, since it permits heating the materials to be welded only at the seam areas and their immediate vicinity, minimizing the heat input.

With the film heated above the Vicar softening temperature, R.F. welding proceeds rapidly and efficiently at low R.F. energy levels, as a result of the high dissipation factor provided by the preheating. The increased dissapation factor is attributable to melting of the crystalline domains. In amorphous form at high temperatures, above the Vicar softening temperature, the polyurethanes have high dissipartion factors. At the low R.F. energy levels, there is no arc formation, no sparking or charring, and bond discontinuities are readily prevented.

The qualitative properties of the weld seams formed by the present invention are consistently and reproducibly excellent. There are also significant reductions in out-of-spec weld joints. Quantitatively, the productivity of the operation is excellent and the energy usage and costs are reduced.

The thermoplastic polyurethane elastomers to which the present invention is applicable are well characterized in the literature, familiar to those of ordinary skill in the art, and are widely available from a number of commercial sources. A variety of such materials are available in medical and food grades. Those of ordinary skill in the art are well able to select appropriate materials for their intended use. The present invention is applicable to such materials.

In the present invention, a combination of dry heat and radio-frequency welding is used to create a seam without breach or deformation. In usage, the method may typically comprise the following steps:

(1) The welding die platen is preheated to a temperature above the Vicat softening temperature of the polyurethane elstomer, typically between 60° C. to 150° C., depending on the nature of the polymer. It is appropriate to keep the temperature below the film deformation temperature. At these temperatures, the die will not stick to the polyurethane film but will provide enough external heat to pre-heat the film and prepare it for welding.

(2) Layers of a thin film are fed through an R.F. heat welder, the two layers ultimately having direct heat transfer contact with the die platen just prior to and suring the welding operation.

(3) The two layers of thin film are subjected to die platen pressure. Pressure, typically in the range of 50 to 80 pounds per square inch (psi), is exerted at least on the seam area of the two layers.

(4) A surge of low power radio-frequency energy is directed by the welder into the seam area of the two layers of film when the pressure from the die platen is exerted on the material. The radio-frequency energy range is generally from 1.0 to 6.0 kw, proportional to the thickness of the thermoplastic film. It is transmitted for a duration of about 1.0 to 2.0 seconds.

The preheated film is excited at the inner molecular surface at this low energy level causing a weld which produces a seam with integrity. Because of the relatively low energy required, the film is not overpowered or overheated, thereby avoiding sparking or burning of the material. By using this method, it is possible to eliminate the excess heat generation of either the standard contact heat sealing machine or the impulse-heat machine. It also eliminates sparking caused by radio-frequency at higher energy levels.

Combining these two operations results in a wrinkle free, thin, weld seam with excellent integrity, only attainable in the past with radio-frequency welding techniques on thicker materials. Preparing the two layers of film for welding by applying heat to raise the temperature above the Vicat softening temperature of the polyurethane film before transmitting radio-frequency energy avoids the slow heating associated with thermoplastic polyurethane elstomers. Less radio-frequency energy is used and thus sparks and burn marks are avoided.

The use of radio-frequency input can be precisely metered, monitored and documented, ensuring seam integrity. This cannot be done with the use of heat sealing.

Thin thermoplastic polyurethane films for certain applications can include a variety of the common forms of compounding components customarily employed with such polymers, including reinforcing fillers, plasticizers or lubricants to give specific properties to the ultimate product. These compounding components may be helpful, for example, to prevent blocking or sticking of the film in unwelded areas not subjected to the seaming operation. In the manufacture of products requiring compounding components, the compounding components are may be combined with the film-forming polymer at the time the film is made. In other circumstances, the additive may be applied as a coating on the surface of the fim prior to welding. In some cases, the additive may be applied to the welded product, although such techniques are often more cumbersome than the preceeding techniques. The additive materials that can be used comprise several types:

(1) antiblocking lubricants are used to prevent sticking between the two polyurethane layers in organ bags, gloves, instrument covers and the like. It makes handling from processing to packaging easier and more reliable. Examples of antiblocking-lubricants are fatty acids, esters, amides, bisamides and silica. The amounts of such lubricants is typically about 0.1 to 2% of the polymer weight.

(2) Antistatic agents may be used for rubber goods to be employed in the electronic industry and with electronic medical appliances and the like. Antistatic properties can be achieved by adding a quaternary ammonium compound, for example, such as the Laurostat® HTS series from PPG Industries, Glycolube®AFA-1 from Lonza, Inc., or Cyastat® LS from American Cyanamid, Inc.

(3) antimicrobials, biocides, and fungistats and the like are used for safety in the health care and food industries for reusable products. Representative examples are N-trichloromethylthio phthalimide, 10,10'-Oxybisphenoxarsine, and 2-N-Octyl-6-isothiazoline.

(4) UV stabilizers and antioxidants may be used, particularly for rubber goods which require particularly long shelf life and for re-usable products such as gloves. An example of an antioxidant is Irsanox® 0.1 to 1% from Geigy, Inc. A useful UV stabilizer is TINUVIN®, also from Geigy.

(5) odorants, deodorants, flavors, pigments, dyes, lakes, opacifiers, brighteners, and the like are used for specific applications.

(6) Radio-opaque fillers are used when it is required to be able to identify a product through x-ray, as for example in locating an organ bag in a body cavity, or as a barrier protection from unintended exposure to incident radiation. Examples of radio-opaque fillers are metallic lead, lead oxides, $BaSO_4$, bismuth oxychloride, bismuth subcarbonate, bismuth trioxide and the oxychlorides, subcarbonates and trioxides of tungsten.

Small amounts of reinforcing fillers, such as silca, carbon black, and the like may be employed. The use of such fillers is well known to the art, and do not interfere with the welding in proportions of less than about 20 to 25% by weight.

While plasticizers are not often employed with the thermoplastic polyurethane elastomers, their use does not impair or impede the present invention.

The present invention has the objective of providing a new method of welding at least two layers of a thin thermoplastic polyurethane elastomer material, with high levels of seam integrity, for the purpose of creating safer and more durable barrier products not previously available or available only at unacceptably high costs.

FIG. 1 is a view of joined polyurethane film layers (10A) and (10B) welded together to form a weld seam (12). Weld seam (12) is created by transmitting radio-frequency energy to preheated film layers (10A) and (10B). In preparation for the welding process, a die platen is preheated prior to joining film layers (10A) and (10B). Once film layers (10A) and (10B) are brought into contact under from 50 to 80 psi from the preheated die platen, the film is preheated by conduction from the heated platen in the area to be welded to a temperature above the Vicar softening temperature, which will typically be from about 150° to 250° F. (65.5 to 121.1 C.) for most polyurethanes. The preheated film temperature should be below the film's melting temperature, preferably about 25° F. below the melting temperature, which varies between different polyurethane materials. The temperature should also be below the film distortion temperature.

Radio-frequency energy of 1.0 to 6.0 kw at 1.0 to 2.0 seconds, depending on the thickness of the film, is then transmitted to film layers (10A) and (10B) to form a weld seam (12) by fusion bonding of the layers at their interface. The welded film layers are then allowed to cool.

Figure 2:
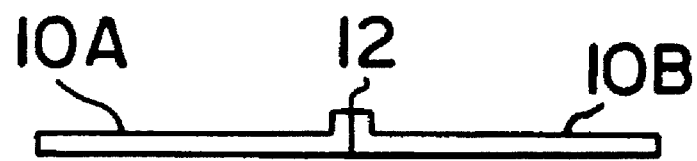
FIG. 2 is a side view of two welded thin film layers of a thermoplastic polyurethane elastomer material.

FIG. 2 is a side view of joined polyurethane film layers (10A) and (10B) of FIG. 1 with weld seam (12). FIG. 2 shows eversion of film layers (10A) and (10B) at weld seam (12). Weld seam (12) has substantially complete continuity and integrity and is without pinholes, holidays or charred edges. Because film layers (10A) and (10B) are preheated, less energy is required at the radio-frequency weld site, thus preventing breach of the polyurethane film. The strength of the weld has be observed to be substantially the same as that of the unwelded film. The span of the weld seam is thus not a critical parameter, although it will usually be at least two, and preferably 3 to 10 times the thickness of the film. Narrower seams make the die more difficult and expensive to fabricate, and make handling of the film feed to the die and platen far more difficult. Wider seams are also possible, but in most cases are pointless and wasteful of the R.F. and platen heating energies and take longer to cool.

Figure 3:
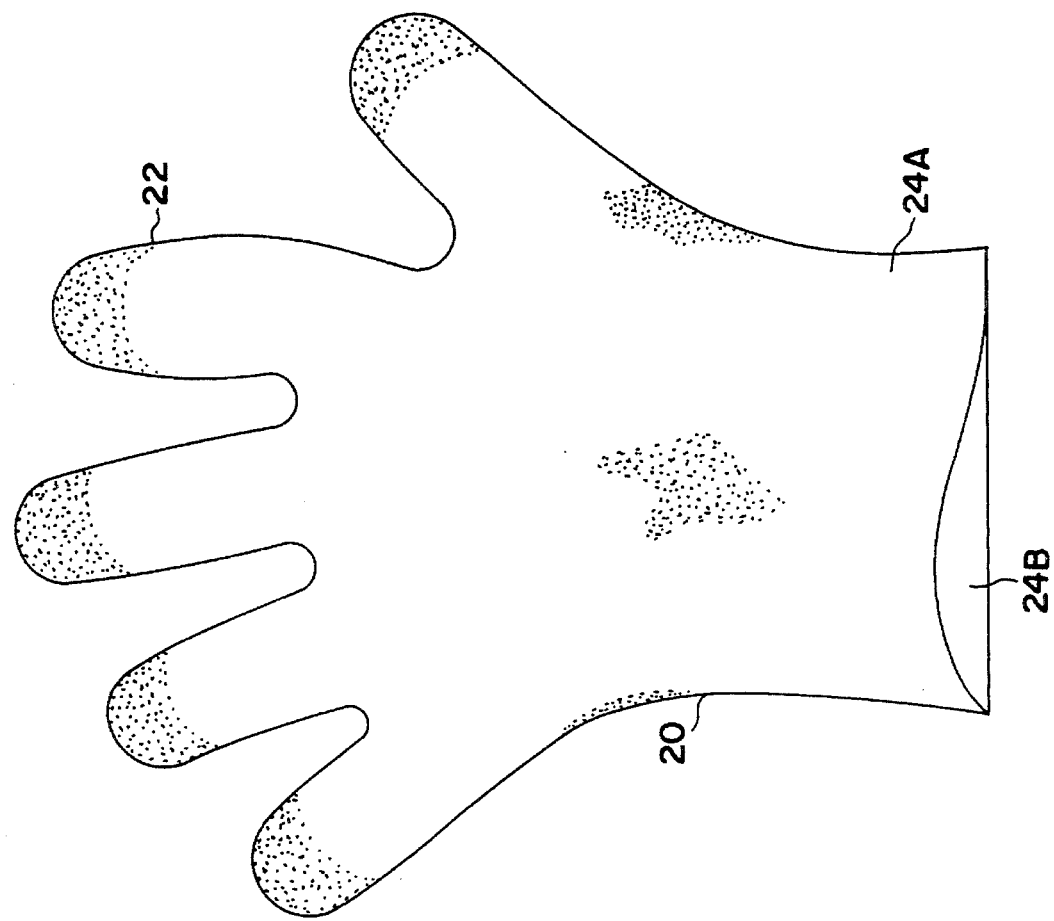
FIG. 3 is a broad view of a thermoplastic polyurethane elastomer glove.

FIG. 3 is a polyurethane glove (20) comprised of polyurethane film layers (24A) and (24B) joined at weld seam (22). Weld seam (22) is located at the finger contours of glove (20) where the two film layers are joined. The preheated die platen takes on the shape of the polyurethane product to be created, in this case, a glove shape. Polyurethane film layers (24A) and (24B) are brought into contact under pressure at the welding site and radio-frequency energy is transmitted thus welding film layers (24A) and (24B) to create weld seam (22).

Figure 4:
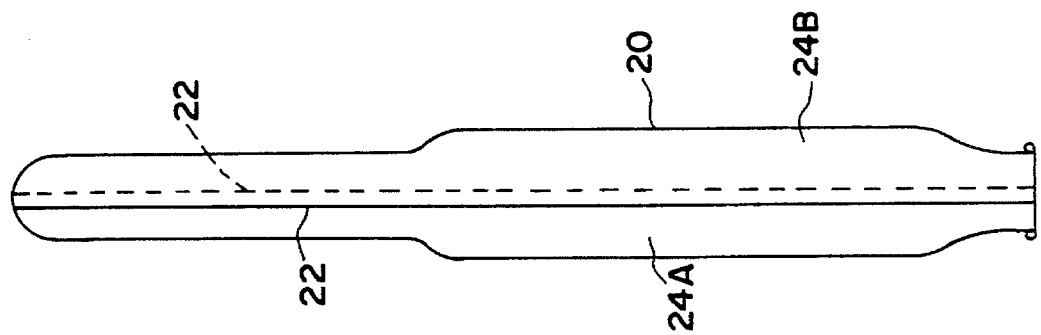
FIG. 4 is a side view of a thermoplastic polyurethane elastomer glove.

FIG. 4 is a side view of glove (20) with polyurethane film layers (24A) and (24B) joined to form weld seam (22).

Figure 5:
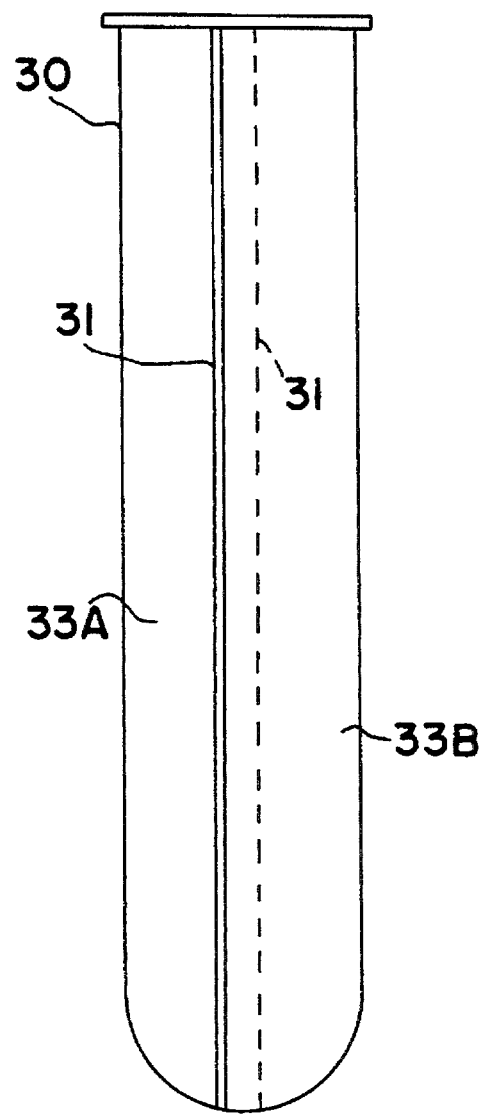
FIG. 5 is a side view of a thermoplastic polyurethane elastomer condom.

FIG. 5 is a male condom (30). Condom (30) is comprised of polyurethane film layers (33A) and (33B) joined at weld seam (31). Polyurethane condoms provide a major breakthrough in barrier protection in preventing the spread of disease as well as in the prevention of an unwanted pregnancy. The polyurethane film is neither porous nor permeable to chemical or microscopic matter. It is a superior material used in barrier protection products when compared to natural rubber latex products and dipped polyurethanes. The weld seam of the present invention has the same strength and integrity as the polyurethane film.

Because of the outstanding properties of the thermoplastic polyurethane films and of the welded seams of the present invention, it is possible to make condoms of thinner films, i.e., on the order of 0.5 to 2 mils, affording particularly enhanced tactile properties and comfort with no diminution of the required barrier protective and prophylactic properties. While the polyurethanes are more expensive than natural rubber, the economies of production in the present invention offset a large component of the materials costs.

As a result of these features, there is likely to be less resistance to the use of condoms by those who dislike the reduced tactile sensations. Resistance to the use of condoms is a major impediment to the prevention of the spread of sexually transmitted diseases and the incidence of unwanted pregnancies.

Figure 6:
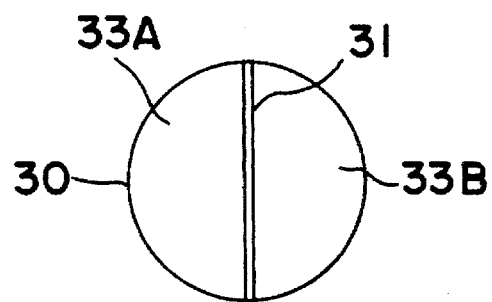
FIG. 6 is a view of the reservoir end of a thermoplastic polyurethane elastomer condom.

FIG. 6 is a view of the reservoir end of male condom (30) with 1.25 mil polyurethane film layers (33A) and (33B) joined to form weld seam (31). Weld seam (31) may be located externally on condom (30). If desired, the condom may be everted after forming, with the seam on the inside of the structure. Thin polyurethane film layers of a thickness of 0.5 to 1.5 mils (0.0127 to 0.0381 mm) or greater may be used.

The method of the present invention may be employed in the fabrication of both male and female condoms. While the safety and effectiveness of female condoms is more sensitive to the specific design of the structure than the male condom, substantially any female condom design can be fabricated by the techniques of the present invention, accruing all the benefits of the improvements of the present invention.

Figure 7:
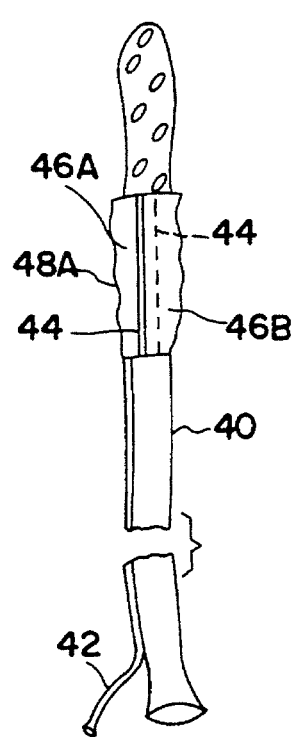
FIG. 7 is a view of an non-inflated thermoplastic polyurethane elastomer balloon cuff of an in-dwelling urinary bladder catheter.

FIG. 7 is a view of a non-inflated polyurethane balloon cuff (48A) of an in-dwelling urinary bladder catheter (40) with film layers (46A) and (46B) joined together at weld seam (44). Balloon cuff (48A) as shown in FIG. 7 is located near the internal end of catheter (40) but may be located at any site on catheter (40) that would bring it in contact with the urethra. To inflate balloon cuff (48A), air is injected into an inflation tube (42) which is internally joined to balloon cuff (48A) Balloon cuff (48A) is comprised of polyurethane film layers (46A) and (46B) at weld seam (44). Catheter (40) is inserted into the urinary bladder by way of the urethra to drain urine during prolonged anesthesia, chronic urinary retention, acute retention, to medically treat the urinary tract or bladder with fluids and medications, as well as other uses. The smooth polyurethane surface of non-inflated balloon cuff (48A) allows it to be passed through the urethra to the bladder with minimum discomfort.

Figure 8:
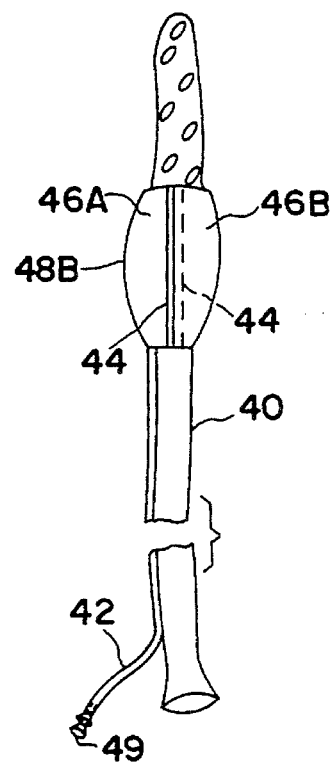
FIG. 8 is an inflated thermoplastic polyurethane elastomer balloon cuff of an in-dwelling urinary bladder catheter.

FIG. 8 is a view of an inflated polyurethane balloon cuff (48B) of an in-dwelling urinary bladder catheter (40) with film layers (46A) and (46B) joined together at weld seam (44). Balloon cuff (48B) is inflated through inflation tube (42) which connects internally to cuff (48B). With cuff (48B) inflated, plug (49) is inserted into tube (42) at the open end of tube (42). Because polyurethane has high strength and integrity, air cannot inadvertently escape through inflated cuff (48B).

Inflatable polyurethane balloon cuffs are applicable to other insertable tubes where balloon cuff seal integrity is required such as in oral and nasal anesthesia endotracheal tubes, venous and arterial catheters and other such tubes.

Angioplasty catheter balloons may be made by the same techniques. The exceptional strength of the polyurethane films of the present invention afford great reliability in such products and the procedures for which they are employed.

Figure 9:
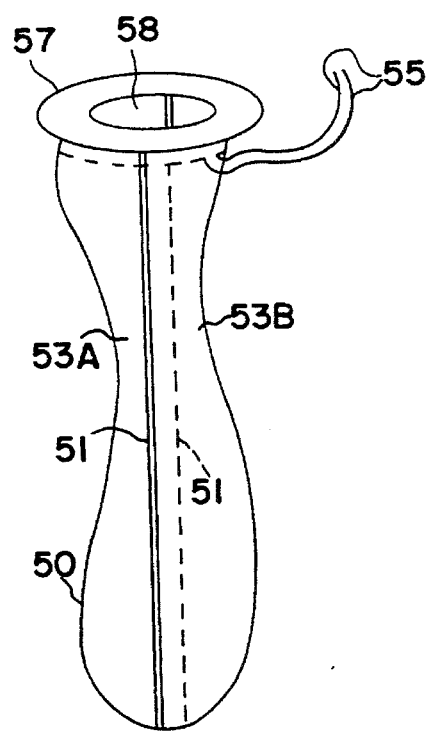
FIG. 9 is a thermoplastic polyurethane elastomer ostomy pouch.

FIG. 9 is an ostomy pouch (50) comprised of film layers (53A) and (53B) joined at weld seam (51) by the process described in the present disclosure. A connecting means (57) of pouch (50) is located at an open-end (58) of pouch (50). Draw pulls (55) are located beneath open-end (58) and are drawn when closing off open end (58) at time of disconnect of connecting means (57). As a durable and leak-proof material, polyurethane is ideal for this use. Weld seam (51) offers maximum protection with seam integrity. Pouch (50) size and shape can be designed for any specific need.

Figure 10:
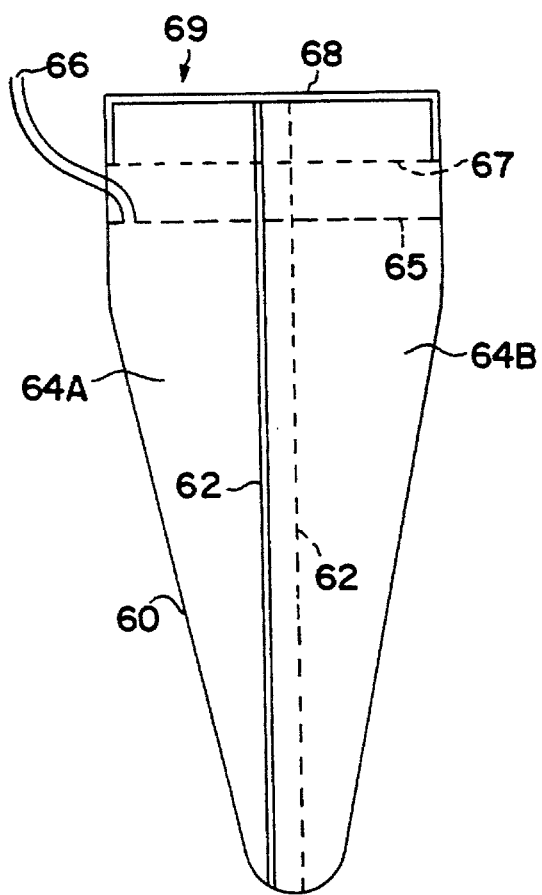
FIG. 10 is a side view of a thermoplastic polyurethane elastomer organ bag.

FIG. 10 is a side view of an organ bag (60) for use in withdrawing tissues excised during edoscopic surgical procedures. The ogan bag is comprised of film layers (64A) and (64B) joined at weld seam (62) through the process described in this disclosure. Bag (60) is funnel shaped with an opening means (68) at open-end (69). A perforations line (67) is located proximal to open-end (69) facilitating separation and removal of opening means (68), wherein opening means (68), following separation, can be removed through an access port in an endoscopic instrument used to place bag (60). A pair of circumferential draw pulls (66) are located beneath and proximal to perforations line (67). When drawn, draw pulls (66) close off open end (69) of bag (60) securing bag contents and facilitating removal from the surgical situs.

Figure 11:
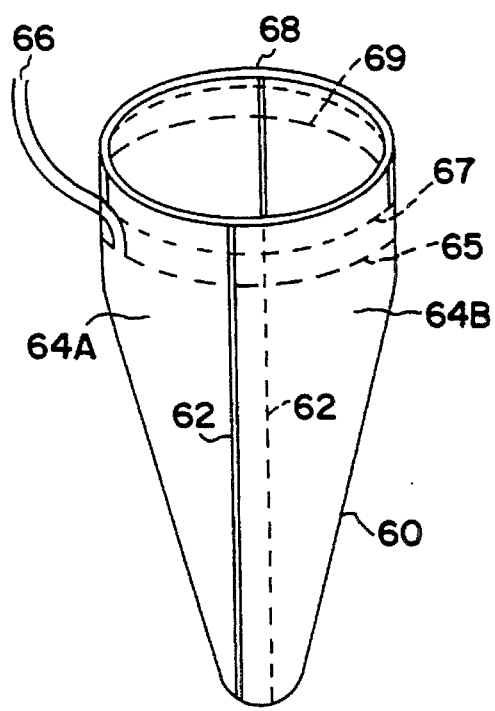
FIG. 11 is an open-top view of a thermoplastic polyurethane elastomer organ bag.

FIG. 11 is an open-top view of organ bag (60) with opening means (68) at open-end (69). Circumferential draw pulls (66) are located on organ bag (60) at line (65) proximal and beneath perforation line (67). The size, shape and dimension of an organ bag is determined by surgical requirements. Polyurethane organ bags are durable, leak-proof, safe and can be fabricated from thin polyurethane material which facilitates removal.

Figure 12:
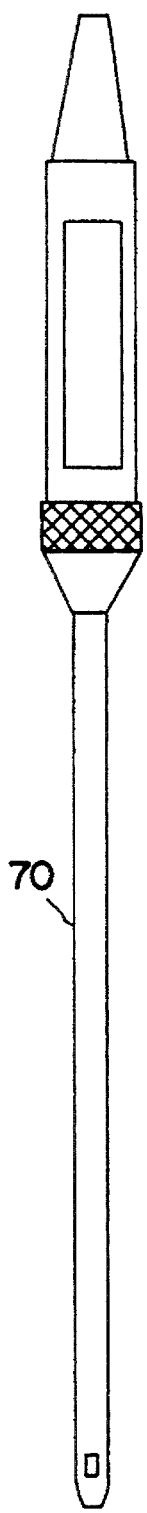
FIG. 12 is a surgical instrument.
Figure 13:
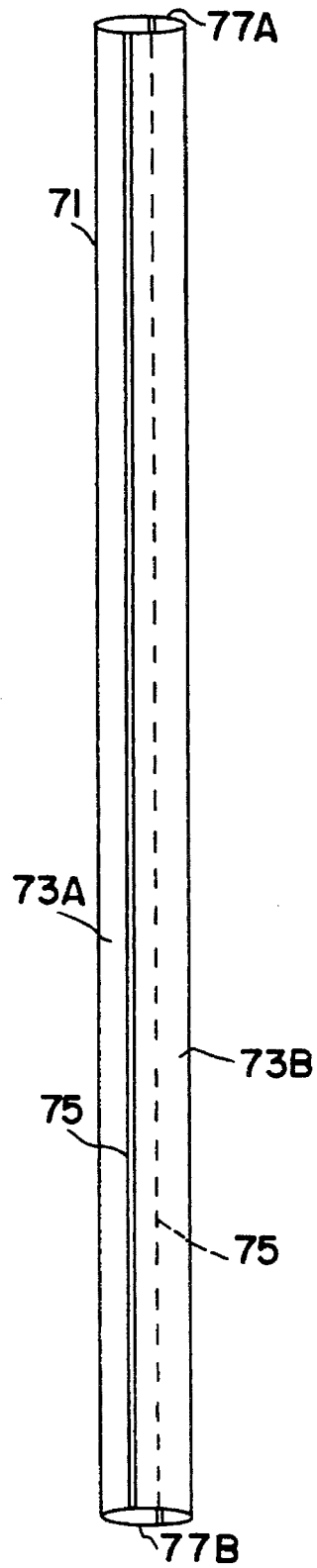
FIG. 13 is a thermoplastic polyurethane elastomer instrument cover.

FIG. 12 illustrates a surgical instrument (70) which is difficult to clean and sterilize. Instruments that cannot be disassembled are frequently difficult or impossible to clean thus exposing surgical patients to contamination with possible infection. To protect a patient from contamination, instrument (70) is placed into an sterile instrument cover (71) through open end (77A). FIG. 13 is a view of instrument cover (71) comprised of polyurethane film layers (73A) and (73B), joined at weld seam (75). Cover (71) has an open-end (77A) and an exit-end (77B) Instrument covers can be made in many shapes and sizes to conform to instrument configurations.

Figure 14:
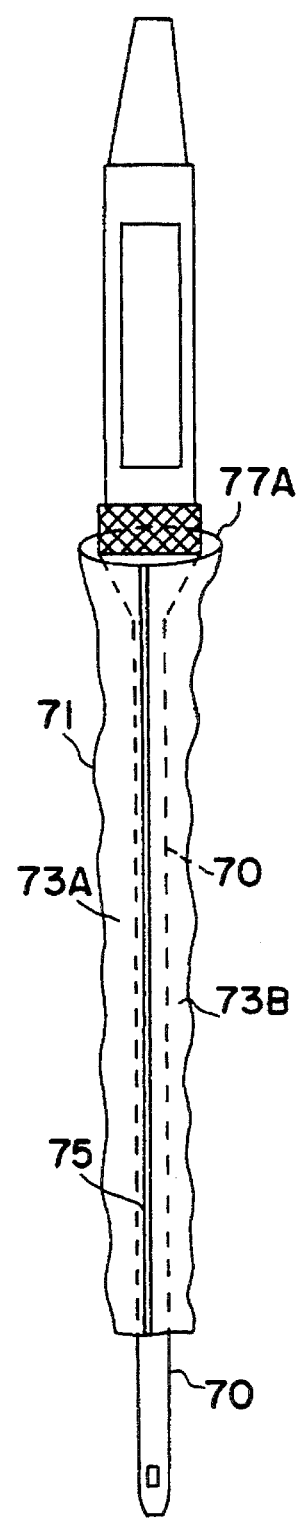
FIG. 14 is a surgical instrument partially inside of a thermoplastic polyurethane elastomer instrument cover.

FIG. 14 is a view of instrument (70) inserted into cover (71) through open-end (77A). The tip end of instrument (70) extends beyond exit-end (77B) for contact with body tissue. In potentially contaminated instruments, a sterile instrument cover offers an extra measure of protection to the patient and security to the surgeon.

EXAMPLE 1

The material to be used for a thermoplastic polyurethane elastomer glove of a thickness of 5 mils (0.127 mm) is selected and fed into an electronic heat welder. The welding die platen is preheated to about 170° F. (76.6° C.). Two layers of thermoplastic polyurethane elastomer-film are then aligned and brought together under pressure of about 80 psi from the die. With the two layers under pressure, and after about 2 seconds preheat time, 4.0 kw of radio-frequency energy is transmitted to the two layers for a period of 2.0 seconds followed by release of the die platen pressure. A weld seam is created without pinholes, holidays, charring or burn marks.

EXAMPLE 2

A 1.5 mils (0.0381 mm) thick thermoplastic polyurethane elastomer film used in the manufacture of a prophylactic condom device is selected. Two layers of the material are aligned and fed into an electronic heat welding machine. The die platen is preheated to 200° F. (93.3° C.). The two layers of film are brought together under 65 psi of pressure from the die platen. With the two layers of film in contact and under pressure, 2.0 kw of radio-frequency energy are transmitted to the film to be welded over a 1.0 second period. The weld seam resulting from the welding process is free of pin holes, holidays, wrinkles or burn marks.

EXAMPLE 3

A 1.2 mils (0.0305 mm) thick thermoplastic polyurethane elastomer film used in the manufacture of a prophylactic condom device is selected. Two layers of the material are aligned and fed into an electronic heat welding machine. The die platen is preheated to 250° F. (121.1° C.). The two layers of film are brought together under 65 psi of pressure from the die. With the two layers of film in contact and under pressure, 1.5 kw of radio-frequency energy are transmitted to the film to be welded over a 1.2 second period. The seam resulting from the welding process is free of pin holes, holidays, wrinkles or burn marks.

EXAMPLE 4

A 0.9 mil (0.0228 mm) thick thermoplastic polyurethane elastomer film used in the manufacture of a prophylactic condom device is selected. Two layers of the material are aligned and fed into an electronic heat welding machine. The die platen is preheated to 250° F. (121.1° C.). The two layers of film are brought together under 55 psi of pressure from the die. With the two layers of film in contact and under pressure, 1.2 kw of radio-frequency energy are transmitted to the film to be welded over a 1.0 second period. The weld seam resulting from the welding process is free of pin holes, holidays, wrinkles or burn marks.

Finally, although the invention has been described with reference of particular means, material and embodiments, it is to be understood that the invention is not limited to the particulars disclosed and extends to all equivalents within the scope of the claims.

What is claimed is:

1. A polyurethane condom comprising:
   A. An elongated tubular structure having one open base end and one dosed distal end, said structure being formed of two generally flat sheets of a polyurethane elastomer film having a thickness of from about 0.5 to 5 mils;
   B. A continuous radio frequency weld joining said two sheets along the periphery thereof starting at said open base end and extending axially to the distal end, extending around the periphery of said distal end, and axially from said distal end to said open base end, said weld having an elongated generally U shape, leaving said open end unwelded, such that the facing surfaces of said sheets define the interior of said condom;
   C. Said radiofrequency weld having a width of two to ten times the thickness of said polyurethane film and a bond strength substantially the same as the unwelded film.

2. The polyurethane condom of claim 1 wherein said condom is a male condom.

3. The polyurethane condom of claim 1 wherein said condom is a female condom.

4. The polyurethane condom of claim 1 wherein said polyurethane film is a thermoplastic polyurethane elastomer.

5. The polyurethane condom of claim 1 wherein said said polyurethane film is a cross-linkable polyurethane elastomer.

6. The polyurethane condom of claim 1 wherein said polyurethane film is a cross-linked polyurethane elastomer.

7. The polyurethane condom of claim 1 wherein said polyurethane film has a thickness of from about 0.5 to about 2 mils.

8. The polyurethane condom of claim 1 wherein said polyurethane film has a thickness of from about 0.5 to about 1.5 mils.

* * * * *